US00PP29506P2

(12) United States Plant Patent
Naisheng et al.

(10) Patent No.: US PP29,506 P2
(45) Date of Patent: Jul. 17, 2018

(54) ***CAMELLIA* PLANT NAMED 'HA242'**

(50) Latin Name: *Camellia japonica X Camellia changii*
Varietal Denomination: HA242

(71) Applicants: Zhong Naisheng, Guangzhou (CN); Yan Danfeng, Guangzhou (CN); Wu Jianjun, Guangzhou (CN)

(72) Inventors: Zhong Naisheng, Guangzhou (CN); Yan Danfeng, Guangzhou (CN); Wu Jianjun, Guangzhou (CN)

(73) Assignee: Palm Eco-Town Development Co. Ltd., Guangzhou (CN)

( * ) Notice: Subject to any disclaimer, the term of this patent is extended or adjusted under 35 U.S.C. 154(b) by 0 days.

(21) Appl. No.: 15/530,357

(22) Filed: Dec. 30, 2016

(51) Int. Cl.
*A01H 5/02* (2018.01)

(52) U.S. Cl.
USPC ..... Plt./245

(58) Field of Classification Search
USPC ..... Plt./245, 244, 243
CPC ..... A01H 5/02; A01H 5/00
See application file for complete search history.

*Primary Examiner* — June Hwu
(74) *Attorney, Agent, or Firm* — C. A. Whealy

(57) ABSTRACT

A new and distinct cultivar of *Camellia* plant named 'HA242', characterized by its sturdy upright plant habit; rapid growth habit; freely branching habit; dense and bushy appearance; leathery dark green-colored leaves; flowering during the summer, autumn and winter; relatively large light red-colored semi-double flowers; and good garden performance.

2 Drawing Sheets

Botanical designation: *Camellia japonica* X *Camellia changii.*

Cultivar denomination: 'HA242'.

BACKGROUND OF THE INVENTION

The present Invention relates to a new and distinct cultivar of *Camellia* plant, botanically known as *Camellia japonica* X *Camellia changii*, and hereinafter referred to by the name 'HA242'.

The new *Camellia* plant is a product of a planned breeding program conducted by the Inventors in Zhaoqing, China. The objective of the breeding program is to create new fast-growing *Camellia* plants that flower year-round and tolerate full sunlight.

The new *Camellia* plant originated from a cross-pollination conducted by the Inventors in October, 2006 in Zhaoqing, China of *Camellia japonica* 'Collettii', not patented, as the female, or seed, parent with an unnamed seedling selection of *Camellia changii*, not patented, as the male, or pollen, parent. The new *Camellia* plant was discovered and selected by the Inventors as a single plant from within the progeny of the stated cross-pollination in a controlled environment in Zhaoqing, China in September, 2011.

Asexual reproduction of the new *Camellia* plant by grafting cuttings onto an unnamed selection of *Camellia gaozhouensis*, not patented, in a controlled greenhouse environment in Zhaoqing, China has shown that the unique features of this new *Camellia* plant are stable and reproduced true to type in successive generations.

SUMMARY OF THE INVENTION

Plants of the new *Camellia* have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'HA242'. These characteristics in combination distinguish 'HA242' as a new and distinct cultivar of *Camellia:*

1. Sturdy upright plant habit.
2. Rapid growth habit.
3. Freely branching habit, dense and bushy appearance.
4. Leathery dark green-colored leaves.
5. Flowering during the summer, autumn and winter.
6. Relatively large light red-colored semi-double flowers.
7. Good garden performance, tolerant to full sunlight conditions.

Plants of the new *Camellia* differ from plants of the female parent, 'Collettii', primarily in the following characteristics:

1. Margins of leaves of plants of the new *Camellia* are not as serrate as margins of leaves of plants of 'Collettii'.
2. Plants of the new *Camellia* flower multiple times during the year whereas plants of plants of 'Collettii' flower once a year.

Plants of the new *Camellia* differ primarily from plants of the male parent selection in the following characteristics:

1. Margins of leaves of plants of the new *Camellia* are serrate whereas margins of leaves of plants of the male parent selection are entire.
2. Plants of the new *Camellia* and the male parent selection differ in flower form as plants of the male parent selection have single-type flowers.

Plants of the new *Camellia* can also be compared to the plants of *Camellia* 'Zhuang Yuan Hong', not patented. In side-by-side comparisons plants of the new *Camellia* differ from plants of the 'Zhuang Yuan Hong' in flowering habit as plants of the new *Camellia* flower multiple times during the year whereas plants of plants of 'Zhuang Yuan Hong' only flower one time each year.

BRIEF DESCRIPTION OF THE PHOTOGRAPHS

The accompanying colored photographs illustrate the overall appearance of the new *Camellia* plant showing the colors as true as it is reasonably possible to obtain in colored reproductions of this type. Colors in the photographs may differ slightly from the color values cited in the detailed botanical description, which accurately describe the colors of the new *Camellia* plant.

The photograph on the first sheet is a side perspective view of a typical flowering plant of 'HA242' grown in a container.

The photograph on the second sheet are close-up view of typical vegetive stems, developing flower buds and developing flowers of 'HA242'.

DETAILED BOTANICAL DESCRIPTION

The aforementioned photographs and following observations and measurements describe plants grown in Zhaoqing, China in an outdoor nursery during the late autumn and under cultural practices typical of commercial *Camellia* production. During the production of the plants, day temperatures averaged 22° C. and night temperatures averaged 18° C. Plants were five years old when the photographs and description were taken. In the following description, color references are made to The Royal Horticultural Society Colour Chart, 2001 Edition, except where general terms of ordinary dictionary significance are used.

Botanical classification: *Camellia japonica* X *Camellia changii* 'HA242'.

Parentage:

*Female, or seed, parent.*—*Camellia japonica* 'Colletii', not patented.

*Male, or pollen, parent.*—Unnamed seedling selection of *Camellia changii*, not patented.

Propagation:

*Type.*—By grafting cuttings onto a rootstock, an unnamed selection of *Camellia gaozhouensis*, not patented.

*Time to produce a rooted young plant, summer.*—About two months days at temperatures about 28° C.

*Time to produce a rooted young plant, winter.*—About two months days at temperatures about 8° C.

Plant description:

*Plant form and growth habit.*—Perennial evergreen shrub; sturdy upright plant habit; vigorous growth habit; rapid growth rate.

*Branching habit.*—Freely branching habit; about three primary lateral branches each with about three to four secondary branches; dense and bushy appearance.

*Plant height.*—About 165 cm.

*Plant diameter, area of spread.*—About 125 cm.

*Lateral branch description.*—Length, secondary branches: About 20 cm. Diameter: About 1.1 cm. Internode length: About 2.2 cm. Strength: Strong. Aspect: Upright to about 45° from vertical. Texture and luster: Smooth, glabrous; slightly glossy; woody with development. Color, young stems: Close to 199B. Color, older stems: Close to N199D.

*Leaf description.*—Arrangement: Alternate, single. Length: About 8.1 cm. Width: About 3.7 cm. Shape: Oblong. Apex: Cuspidate. Base: Cuneate. Margin: Serrate. Venation pattern: Pinnate, arcuate. Texture and luster, upper surface: Smooth, glabrous; leathery; moderately glossy. Texture and luster, lower surface: Smooth, glabrous; leathery; matte. Color: Developing leaves, upper surface: Close to 146A. Developing leaves, lower surface: Close to 146B. Fully expanded leaves, upper surface: Close to 147A; venation, close to 143B; color does not change with the seasons. Fully expanded leaves, lower surface: Close to 146A; venation, close to 144A; color does not change with the seasons.

*Petioles.*—Length: About 1.1 cm. Diameter: About 2.5 mm. Texture and luster, upper and lower surfaces: Smooth, glabrous; matte. Color, upper surface: Close to 146A. Color, lower surface: Close to 146B.

Flower description:

*Flower arrangement and appearance.*—Semi-double rotate flowers, flowers terminal and axillary; freely flowering habit with usually about ten flowers and flower buds developing per plant; flowers face upright to outwardly to nodding.

*Natural flowering season.*—Plants of the new *Camellia* flower during the summer, autumn and winter in Zhaoqing, China.

*Postproduction longevity.*—Plants maintain good flower substance for about eight to ten days on the plant; flowers persistent.

*Fragrance.*—None detected.

*Flower diameter.*—Relatively large, about 8.7 cm.

*Flower depth.*—About 4.2 cm.

*Flower buds.*—Length: About 3.2 cm. Diameter: About 2.1 cm. Shape: Ovoid. Texture and luster: Smooth, glabrous; glossy. Color: Close to N144A.

*Petals.*—Quantity and arrangement: About 28 imbricate petals arranged in numerous whorls. Length: About 4.1 cm. Width: About 3.2 cm. Shape: Broadly obovate. Apex: Obcordate. Base: Cuneate. Margin: Entire; slightly undulate. Texture and luster, upper and lower surfaces: Smooth, glabrous; matte. Color: When opening, upper and lower surfaces: Close to 50A. Fully opened, upper surface: Close to 52A; venation, close to 53C; color does not change with development. Fully opened, lower surface: Close to 52A; venation, close to 53B; color does not change with development.

*Petaloids.*—Quantity and arrangement: About four petaloids at the center of the flower. Length: About 2.1 cm. Width: About 1.1 cm. Shape: Obovate. Apex: Obcordate. Base: Cuneate. Margin: Entire; moderately undulate. Texture and luster, upper and lower surfaces: Smooth, glabrous; matte. Color: When opening, upper and lower surfaces: Close to 53C. Fully opened, upper surface: Close to 54A; venation, close to 54A; color becoming closer to 51A with development. Fully opened, lower surface: Close to 55A; venation, close to 54A; color becoming closer to 51A with development.

*Sepals.*—Quantity and arrangement: About six imbricate sepals arranged in a shallow cup-shaped calyx. Length: About 1.6 cm. Width: About 1.4 cm. Shape: Rounded. Apex: Obtuse. Base: Rotund. Margin: Entire. Texture and luster, upper and lower surfaces:

Smooth, glabrous; leathery; moderately glossy. Color: When opening, upper surface: Close to 145C. When opening, lower surface: Close to 145B. Fully opened, upper surface: Close to 144C. Fully opened, lower surface: Close to 145A.

*Peduncles*.—Length: About 5 mm. Diameter: About 5 mm. Aspect: About 20° to 30° from stem axis. Strength: Strong. Texture and luster: Smooth, glabrous; matte. Color: Close to 146A.

*Reproductive organs*.—Androecium: Quantity per flower: About twelve. Filament length: About 3.1 cm. Filament color: Close to 38A. Anther shape: Oblong. Anther size: About 2.1 mm by 1.3 mm. Anther color: Close to 6A. Pollen amount: Scarce. Pollen color: Close to 6A. Gynoecium: Quantity of pistils per flower: Bi-parted. Pistil length: About 2.2 cm. Style length: About 2.1 cm. Style color: Close to 4C. Stigma color: Close to 4B. Ovary color: Close to 4D.

*Fruits and seeds*.—Fruit and seed production have not been observed on plants of the new *Camellia*.

Garden performance: Plants of the new *Camellia* have been observed have good garden performance and to tolerate rain, wind, full sunlight and temperatures ranging from about −10° C. to about 40° C.

Disease & pest resistant: Plants of the new *Camellia* have not been observed to be resistant to pathogens and pests common to *Camellia* plants.

It is claimed:

1. A new and distinct cultivar of *Camellia* plant named 'HA242' as illustrated and described.

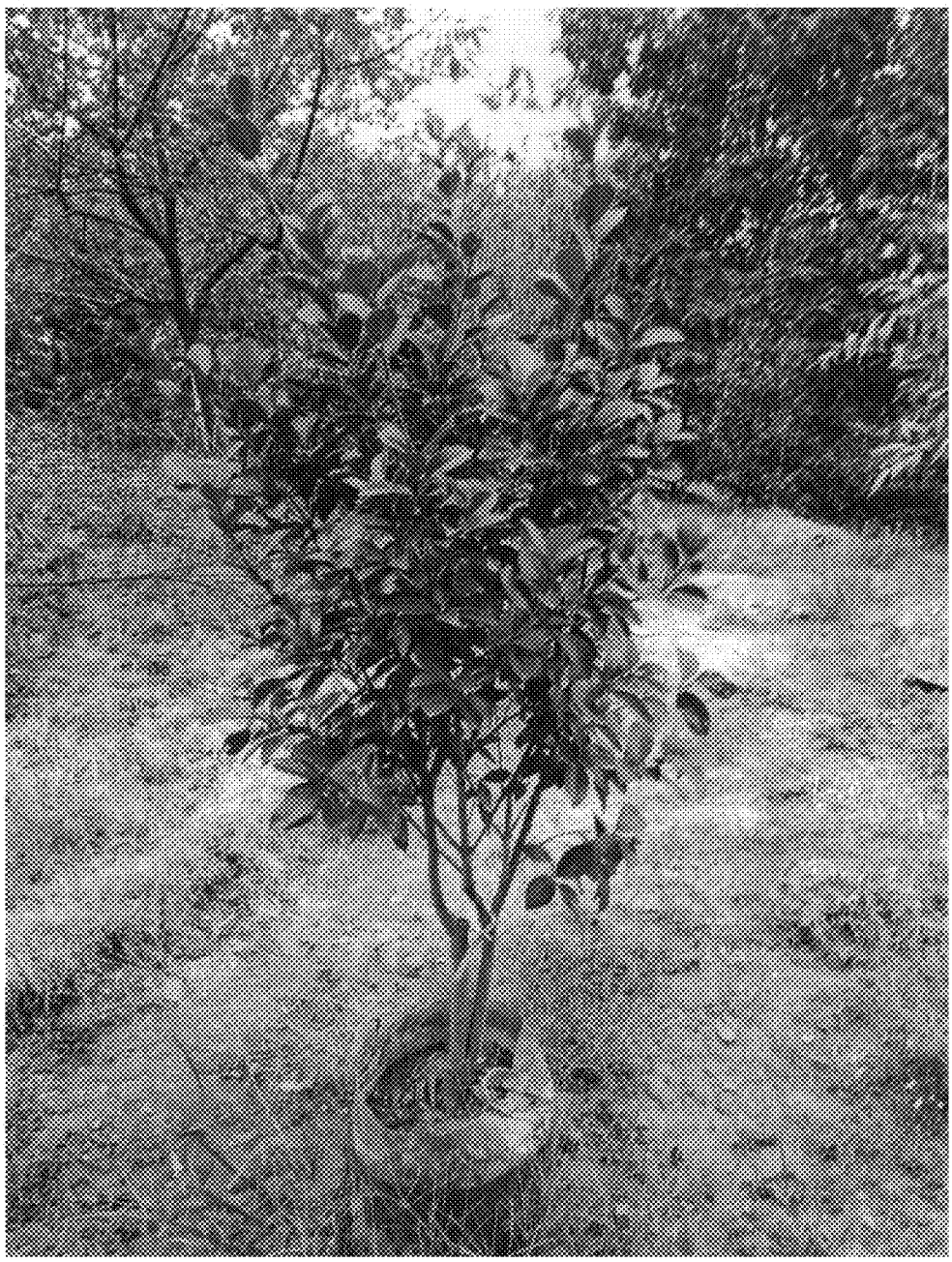

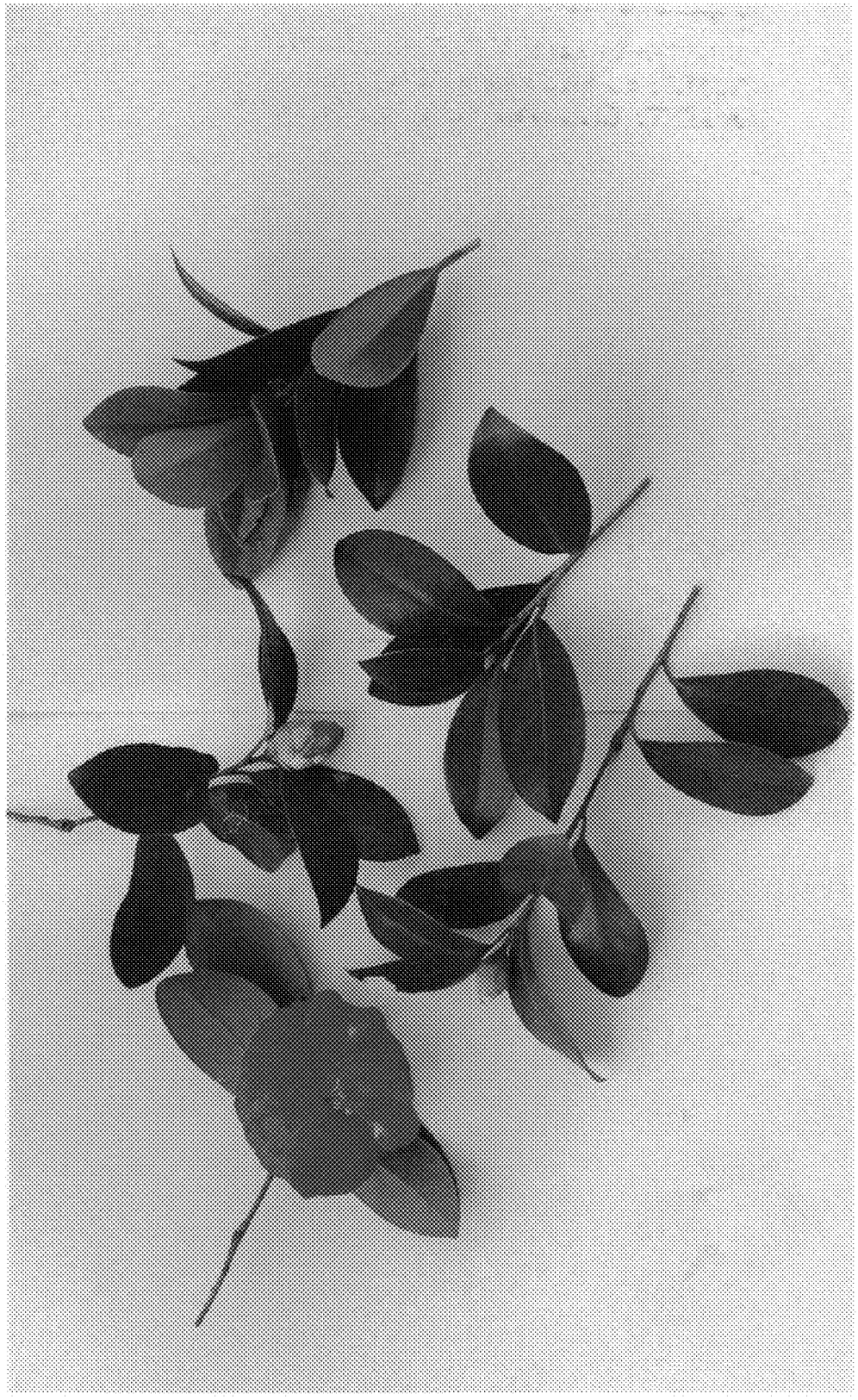

* * * * *